US012263264B2

(12) United States Patent
Gonzalez

(10) Patent No.: US 12,263,264 B2
(45) Date of Patent: Apr. 1, 2025

(54) TROLLEY WITH UV SANITATION

(71) Applicant: B/E Aerospace, Inc., Winston Salem, NC (US)

(72) Inventor: Arnau Castillo Gonzalez, Maarssen (NL)

(73) Assignee: B/E AEROSPACE, INC., Winston-Salem, NC (US)

( * ) Notice: Subject to any disclaimer, the term of this patent is extended or adjusted under 35 U.S.C. 154(b) by 0 days.

(21) Appl. No.: 18/442,961

(22) Filed: Feb. 15, 2024

(65) Prior Publication Data
US 2024/0181101 A1   Jun. 6, 2024

Related U.S. Application Data

(62) Division of application No. 17/326,932, filed on May 21, 2021, now Pat. No. 11,925,716.

(60) Provisional application No. 63/029,948, filed on May 26, 2020, provisional application No. 63/028,988, filed on May 22, 2020.

(51) Int. Cl.
*A61L 2/10* (2006.01)
*A61L 2/26* (2006.01)
*B62B 3/02* (2006.01)
*B62B 5/00* (2006.01)

(52) U.S. Cl.
CPC .................. *A61L 2/10* (2013.01); *A61L 2/26* (2013.01); *B62B 3/02* (2013.01); *B62B 5/0036* (2013.01); *B62B 5/0053* (2013.01); *A61L 2202/11* (2013.01); *A61L 2202/122* (2013.01);
(Continued)

(58) Field of Classification Search
CPC ......... B62B 3/02; B62B 2202/67; A61L 2/10; A61L 2/26; A61L 2202/122; A61L 2202/16; A61L 2202/26; A61L 2202/50
See application file for complete search history.

(56) References Cited

U.S. PATENT DOCUMENTS 4,135,269 A * 1/1979 Marston ................. A47L 13/58
15/264
4,877,964 A * 10/1989 Tanaka ..................... A23L 3/28
250/455.11
(Continued)

FOREIGN PATENT DOCUMENTS

CN       108853546 A      11/2018
CN       209980351 U       1/2020
(Continued)

OTHER PUBLICATIONS

Extended European Search Report for European Patent Application No. EP 21175745.5, dated Oct. 28, 2021.
(Continued)

*Primary Examiner* — Jeffrey J Restifo
(74) *Attorney, Agent, or Firm* — SNELL & WILMER L.L.P.

(57) ABSTRACT

A trolley assembly includes a trolley housing defining an internal cavity. The assembly includes at least one ultraviolet (UV) illumination system contained within the internal cavity in a stowed position. The UV illumination system configured and adapted to extend outward from the internal cavity in a deployed position. The trolley assembly includes a battery in electrical communication with the at least one UV illumination system.

8 Claims, 2 Drawing Sheets

(52) U.S. Cl.
CPC ....... *A61L 2202/16* (2013.01); *A61L 2202/26* (2013.01); *B62B 2202/50* (2013.01)

(56) References Cited

U.S. PATENT DOCUMENTS

| | | | | |
|---|---|---|---|---|
| 5,397,010 | A * | 3/1995 | Gibot | F25D 3/125 |
| | | | | 312/236 |
| 7,887,316 | B2 | 2/2011 | Cox | |
| 9,107,973 | B1 * | 8/2015 | Robinson | A61L 2/22 |
| 9,114,183 | B2 * | 8/2015 | Campagna | A61L 2/10 |
| 9,586,365 | B2 | 3/2017 | Chen et al. | |
| 9,675,984 | B1 * | 6/2017 | Sotelo | B05B 9/007 |
| 9,907,870 | B2 * | 3/2018 | Boodaghians | H10K 50/00 |
| 9,968,697 | B1 * | 5/2018 | Philipps | A61L 2/24 |
| 10,387,097 | B2 * | 8/2019 | Shah | G09G 3/2092 |
| 10,780,504 | B2 | 9/2020 | Xiao et al. | |
| 11,925,716 | B2 * | 3/2024 | Gonzalez | A61L 2/10 |
| 2005/0023483 | A1 * | 2/2005 | Fenc | A61L 2/10 |
| | | | | 250/455.11 |
| 2005/0212239 | A1 * | 9/2005 | Carter | A23L 3/28 |
| | | | | 280/47.35 |
| 2012/0305787 | A1 * | 12/2012 | Henson | A61L 2/10 |
| | | | | 250/492.1 |
| 2013/0333550 | A1 * | 12/2013 | Jacobsen | B64D 11/04 |
| | | | | 89/36.09 |
| 2014/0241941 | A1 * | 8/2014 | Kreitenberg | A61L 2/10 |
| | | | | 250/492.1 |
| 2014/0265048 | A1 | 9/2014 | Burris et al. | |
| 2014/0265049 | A1 | 9/2014 | Burris et al. | |
| 2015/0118107 | A1 * | 4/2015 | Sunkara | A61L 2/10 |
| | | | | 250/455.11 |
| 2017/0290936 | A1 * | 10/2017 | Stibich | A61L 2/10 |
| 2018/0256764 | A1 * | 9/2018 | Kreitenberg | A61L 9/20 |
| 2018/0272017 | A1 * | 9/2018 | Stibich | A61L 2/24 |
| 2019/0084235 | A1 | 3/2019 | Roure Pastor et al. | |
| 2020/0346406 | A1 | 11/2020 | Ewald | |
| 2021/0010849 | A1 | 1/2021 | Laws et al. | |
| 2021/0346541 | A1 * | 11/2021 | Callahan | A61L 2/10 |
| 2021/0361799 | A1 * | 11/2021 | Gonzalez | B62B 5/0036 |
| 2022/0023459 | A1 * | 1/2022 | Colletti | A61L 2/10 |
| 2022/0024606 | A1 * | 1/2022 | Freyling | B64F 5/30 |
| 2022/0047734 | A1 * | 2/2022 | Michalakos | A61L 2/10 |
| 2022/0055304 | A1 | 2/2022 | Gueller | |
| 2022/0080074 | A1 * | 3/2022 | Braverman | A61L 9/20 |
| 2022/0088241 | A1 * | 3/2022 | Braverman | A61L 9/20 |
| 2022/0096690 | A1 * | 3/2022 | Tan Hiang Kiat | A61L 2/22 |
| 2022/0193288 | A1 * | 6/2022 | Fanourgiakis | B60S 3/04 |
| 2022/0194008 | A1 | 6/2022 | Van Iersel et al. | |
| 2022/0241441 | A1 * | 8/2022 | Hickey | A61L 2/24 |
| 2022/0296758 | A1 * | 9/2022 | DeGennaro | A61L 2/07 |
| 2022/0395863 | A1 | 12/2022 | Singh | |
| 2023/0011573 | A1 * | 1/2023 | Levitt | A61L 2/10 |
| 2023/0042650 | A1 * | 2/2023 | Ross | A61L 2/22 |
| 2023/0106767 | A1 * | 4/2023 | Ramanand | A61L 2/10 |
| | | | | 422/300 |
| 2023/0123481 | A1 * | 4/2023 | Burke | A61L 2/24 |
| | | | | 422/1 |
| 2023/0149583 | A1 * | 5/2023 | Aly | A61L 2/24 |
| | | | | 422/105 |
| 2023/0310684 | A1 * | 10/2023 | Rister | B64D 11/00 |
| | | | | 422/24 |
| 2023/0375199 | A1 * | 11/2023 | Delmiglio | F24F 3/167 |
| 2024/0181109 | A1 * | 6/2024 | Slycke | A61L 2/24 |
| 2024/0252703 | A1 * | 8/2024 | Slycke | A61L 2/24 |

FOREIGN PATENT DOCUMENTS

| | | |
|---|---|---|
| CN | 111588877 A | 8/2020 |
| CN | 213674136 U | 7/2021 |
| EP | 3643326 | 4/2020 |
| EP | 3643326 A1 | 4/2020 |
| WO | 2019068189 A1 | 4/2019 |
| WO | 2019143699 A1 | 7/2019 |

OTHER PUBLICATIONS

Ress, Adam, "Honeywell to Introduce Fast, Affordable Ultraviolet Cleaning System for Airplane Cabins," Jun. 9, 020, available at: https://aerospace.honeywell.com/en/leam/about-us/press-release/2020/06/uv-cleaning-system-for-irplane-cabins.

* cited by examiner

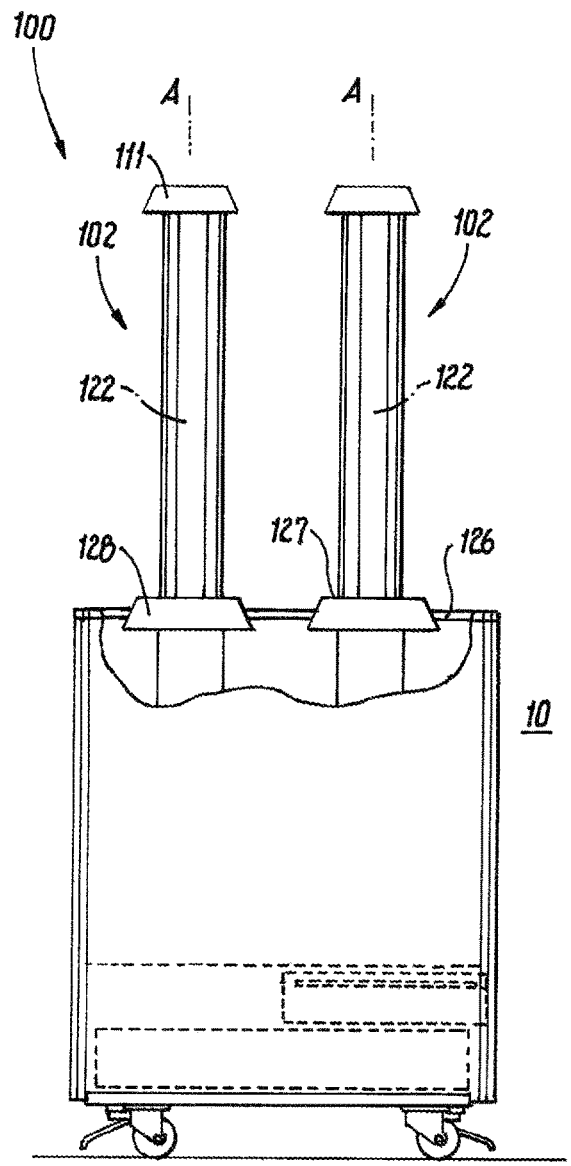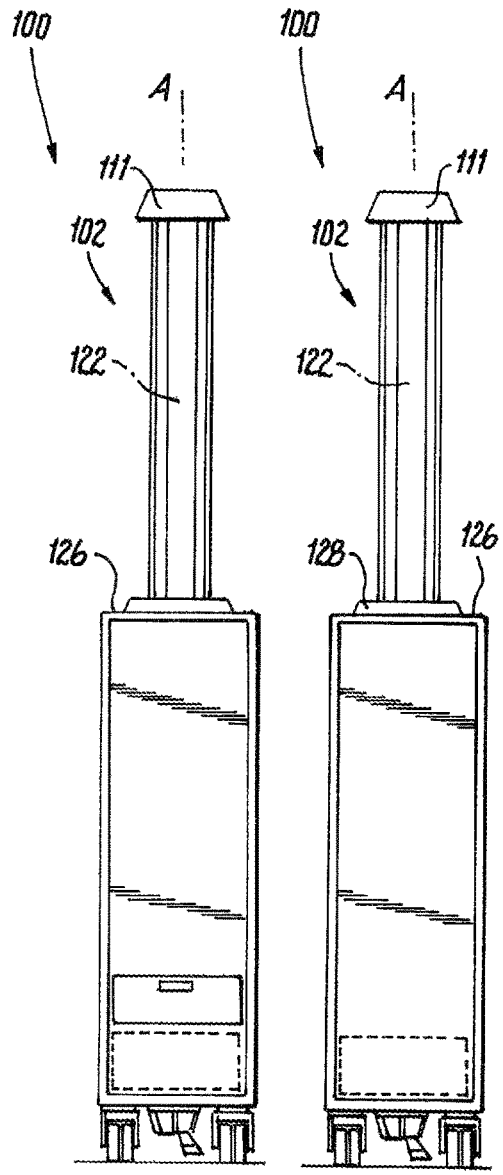
Fig. 3   Fig. 4A   Fig. 4B

TROLLEY WITH UV SANITATION

CROSS-REFERENCE TO RELATED APPLICATIONS

This application is a divisional of U.S. patent application Publication Ser. No. 17/326,932, which claims priority to and benefit of U.S. Provisional Application No. 63/028,988, filed May 22, 2020, and to U.S. Provisional Application No. 63/029,948, filed May 26, 2020, the entire contents of both applications are herein incorporated by reference in their entirety.

BACKGROUND

1. Field

The present disclosure relates generally to disinfection and sanitization of cabin areas and protective gear such as face masks, and more particularly to such disinfection and sanitization aboard aircraft.

2. Description of Related Art

The COVID-19 outbreak has raised the demands of disinfection in common-carrier cabins, such as those of aircrafts and trains, and the objects within. Customers, ground personnel and cabin crew may wear more protective gear but possible contamination of surfaces through the aircraft can still happen during in and out boarding processes and flight.

There is an ongoing need for improved systems and methods to decontaminate common areas such as cabin seating areas, as well as loose items including masks and other protective equipment, aboard aircraft providing service to the crew, ground personnel, and passengers. This disclosure provides a solution for this need.

SUMMARY

A trolley assembly includes a trolley housing defining an internal cavity. The assembly includes at least one ultra-violet (UV) illumination system contained within the internal cavity in a stowed position. The UV illumination system configured and adapted to extend outward from the internal cavity in a deployed position. The trolley assembly includes a battery in electrical communication with the at least one UV illumination system.

The trolley assembly can include a drawer. The drawer can be configured and adapted to slide between a stowed position within the internal cavity of the trolley housing and an extended position. The trolley assembly can include a second UV illumination system mounted in the trolley housing above the drawer to illuminate surfaces of objects in the drawer with UV illumination. The UV illumination system can include at least one UVC illuminator configured to emit UVC illumination with a wavelength ranging from 200 to 280 nm. The drawer can be large enough to accommodate a plurality of personal protective equipment (PPE) masks.

The UV illumination system can include at least one UVC illuminator configured to emit UVC illumination with a wavelength ranging from 200 to 280 nm. The UV illumination system can include at least one UVC illuminator configured to emit UVC illumination with a wavelength of 222 nm. The UV illumination system can define a longitudinal axis and can include at least one UVC illuminator configured and adapted to emit UVC light in any direction required to achieve the highest disinfection and sanitization efficiency. The UV illumination system can define a longitudinal axis and can include at least one UVC illuminator configured and adapted to emit UVC light in any direction to reach most probable touch surfaces of the cabin.

The trolley assembly can include a plurality of wheels operatively connected to the trolley housing, and at least one motor operatively connected to at least one of the plurality of wheels. The at least one motor can be configured and adapted to drive at least one of the plurality of wheels. The trolley assembly can include a processing system operatively coupled to each respective motor to control the motion of the trolley. The trolley assembly can include a plurality of wheels operatively connected to the trolley housing, and a plurality of motors. Each of the plurality of motors can be operatively connected to a respective one of the plurality of wheels. Each of the plurality of motors can be configured and adapted to drive the respective one of the plurality of wheels.

In accordance with another aspect, a method includes moving at least one ultra-violet (UV) illumination system between a stowed position within an internal cavity of a trolley housing to a deployed position extended from the internal cavity. The method includes activating the UV illumination system in the extended position to disinfect an area external to the internal cavity of the trolley.

Activating the UV illumination system can include activating the UV illumination system for a threshold period of time. The method can include charging the UV illumination system with a battery when the illumination system is in the stowed position. Moving the at least one UV illumination system can include lowering the UV illumination system below a top surface of the trolley along a longitudinal axis to the stowed position. Moving the at least one UV illumination system can include elevating the UV illumination system above a top surface of the trolley along a longitudinal axis to the deployed position. The method can include activating at least one motor operatively connected to at least one wheel of the trolley housing to move the trolley housing along an aisle. The method can include activating a second UV illumination system mounted in the trolley housing above a drawer to illuminate surfaces of objects in the drawer with UV illumination. Activating the UV illumination system can include activating the UV illumination system to emit UVC illumination with a wavelength ranging from 200 to 280 nm. Activating the UV illumination system can include activating the UV illumination system to emit UVC illumination with a wavelength of 222 nm.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIG. 3 is a schematic side view of the trolley assembly of FIG. 1, showing the UV illumination systems in the deployed position;

FIG. 4A is a schematic front view of the trolley assembly of FIG. 1, showing the UV illumination systems in the deployed position; and FIG. 4B is a schematic rear view of the trolley assembly of FIG. 1, showing the UV illumination systems in the deployed position.

DETAILED DESCRIPTION

Figure 1:
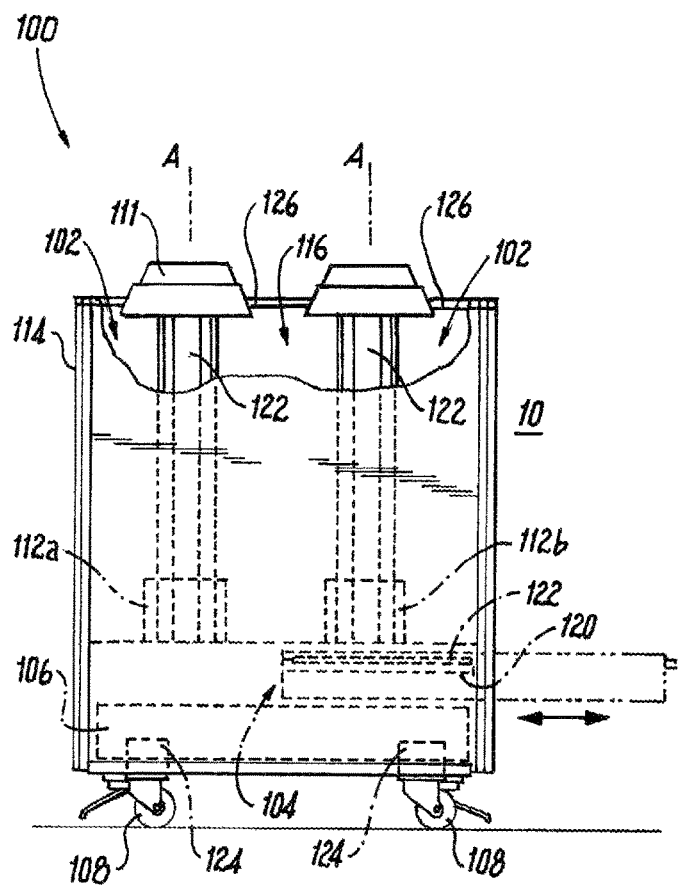
FIG. 1 is a schematic side view of an embodiment of a trolley assembly constructed in accordance with the present disclosure, showing a plurality of ultra-violet (UV) illumination systems.

Reference will now be made to the drawings wherein like reference numerals identify similar structural features or aspects of the subject disclosure. For purposes of explanation and illustration, and not limitation, a partial view of an embodiment of a system in accordance with the disclosure is shown in FIG. 1 and is designated generally by reference character 100. Other embodiments of systems in accordance with the disclosure, or aspects thereof, are provided in FIGS. 2A-4B, as will be described. The systems and methods described herein can be used to disinfect and decontaminate cabin areas on demand, e.g. a cabin 10 within aircraft or other transport devices, such as trains, ships, or the like.

As shown in FIGS. 1 and 3, a trolley assembly 100 includes a trolley housing 114 defining an internal cavity 116. The trolley housing 114 includes a top surface 126 with an opening 127 and a neck portion 128. The assembly includes two ultra-violet (UV) illumination system 102 contained within the internal cavity 116 in a stowed position. Each UV illumination system 102 configured and adapted to extend outward from the internal cavity 116 in a deployed position, shown in FIGS. 3 and 4A-4B. Each illumination system 102 can include a cap portion 111 configured and adapted to mate with the neck portion 128 of the opening when the illumination system 102 is in the stowed position. Those skilled in the art will readily appreciate that any number of UV illumination systems 102 could be used depending on the size of the trolley housing 114. The trolley assembly 100 includes lift mechanisms 112a and 112b, such as a scissor lift mechanisms, to raise respective UV illumination systems 102. These mechanisms 112a and 112b can be electronically or manually driven. The trolley assembly 100 includes a battery 106 in electrical communication with the UV illumination systems 102. Each UV illumination system 102 includes at least one UVC illuminator 122 configured to emit UVC illumination with a wavelength ranging from 200 to 280 nm. For example, if the UV illumination systems 102 are being used in the presence of passengers or crew, 222 nm UVC can be used. Alternatively, depending on material tolerances within the cabin, a higher wavelength, such as 254 nm can be used if passengers and crew would not be present (e.g. when the trolley assembly 100 moves autonomously). Each UV illumination system 102 defines a respective longitudinal axis A. The UVC illuminators 122 in each UV illumination system 102 are configured and adapted to emit UVC light in an unlimited amount of directions, sufficient to reach most probable touch surfaces of the cabin. Each UVC illuminator 122 can include a cluster of high density UVC lights. Those skilled in the art will readily appreciate that, in some embodiments, each UV illumination system 102, e.g., each tower, can include multiple UVC illuminators.

Figure 2A:
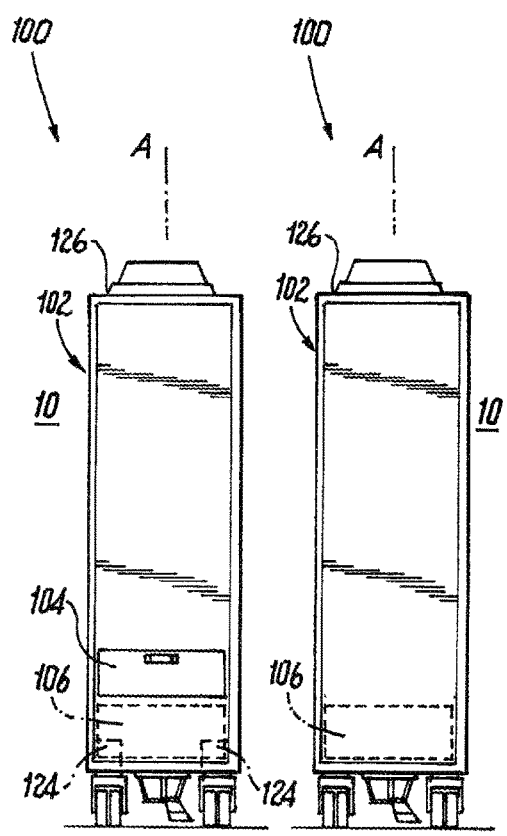
FIG. 2A is a schematic front view of the trolley assembly of FIG. 1, showing a PPE drawer.
Figure 2B:
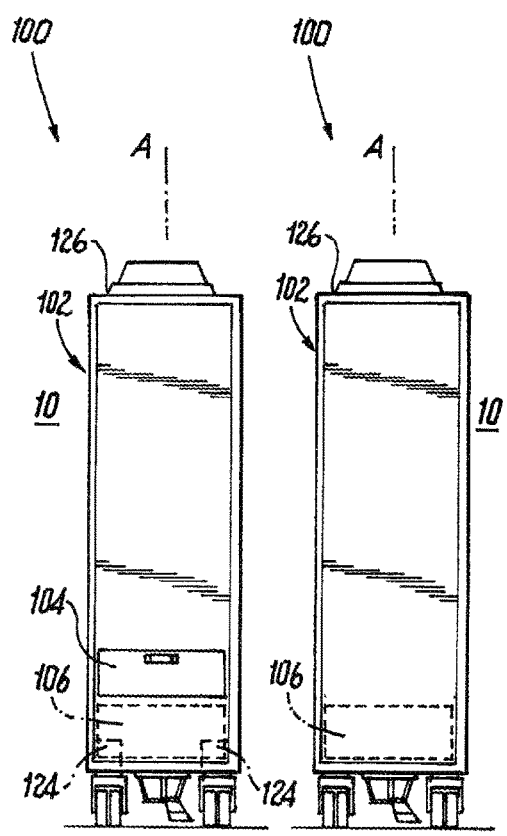
FIG. 2B is a schematic rear view of the trolley assembly of FIG. 1, showing a battery operatively connected to the UV illumination systems.

With reference now to FIGS. 1-2B, the trolley assembly 100 includes a plurality of wheels 108 operatively connected to the trolley housing 114. In the embodiment of FIGS. 1-2B, respective motors 124 are operatively connected to each wheel 108. Those skilled in the art, however, will readily appreciate that motors 124 may not be needed, as the trolley assembly 100 can be manually pushed by a cabin attendant. Each respective motor 124 is configured and adapted to drive each wheel 108. It is also contemplated that, in some embodiments, a single motor 124 could drive a set of wheels, e.g. a pair of front wheels, or all four wheels. The trolley assembly 100 includes a processing system operatively coupled to each respective motor 124 to control the motion of the trolley assembly 100. When used in an aircraft, ship, train or other mode of transport, the trolley assembly 100 can be stowed either at an on-ground operations center (off-wing or off-board) or within the transport vessel, e.g. an aircraft cabin galley monument, or the like. In both cases, the battery 106 (with different requirements depending on whether it is stowed-in/off wing) is used to supply power to at least one UV illumination system 102. As well, it is contemplated that the battery 106 can be charged either off-wing or off-board, or within the transport vessel. The off-/on-wing option provides flexibility in how and when disinfecting and decontaminating will take place.

With continued reference to FIG. 1, the trolley assembly 100 includes a drawer 104. The drawer 104 is configured and adapted to slide between a stowed position within the internal cavity 116 of the trolley housing 114 and an extended position (shown schematically by the broken line drawer in FIG. 1). The trolley assembly 100 includes another UV illumination system 120 mounted in the trolley housing 114 above the drawer 104 to illuminate surfaces of objects in the drawer 104 with UV illumination. The UV illumination system 120 includes at least one UVC illuminator 122, e.g. a cluster of high density UVC lights, configured to emit UVC illumination with a wavelength ranging from 200 to 280 nm. The drawer 104 is large enough to accommodate a plurality of personal protective equipment (PPE) masks.

A method includes moving a trolley assembly, e.g. trolley assembly 100, out of its stowed place. The method includes moving UV illumination systems, e.g. UV illumination systems 102, between a stowed position within an internal cavity, e.g. internal cavity 116 of a trolley housing, e.g. trolley housing 114, as shown in FIGS. 1 and 2A-2B, to a deployed position extended from the internal cavity, as shown in FIGS. 3 and 4A-4B. Moving the illumination systems 102 includes lifting each system 102 with a respective lift mechanism, e.g. a scissor lift mechanism 112a and 112b, which can be electric or non-electric. The method includes activating the UV illumination system, e.g. turning the UVC light on, in the extended position to disinfect an area external to the internal cavity of the trolley, for example, a cabin 10. The trolley assembly 100 is then manually or electrically driven through the cabin corridor and disinfects the cabin. The system 100 can be used after all customers are out to provide a clean cabin, e.g. during the time it would take to change-over a plane between flights.

Activating the UV illumination system includes activating the UV illumination system for a threshold period of time, for example, for a period of time while the trolley is positioned in one spot of the cabin or in a given stretch of area within the cabin. The method can include, in some embodiments, de-activating the UV illumination system while moving the trolley to another spot of the cabin and then re-activating the UV illumination system once the trolley as reached the other spot in the cabin. The method includes charging the UV illumination system with a battery, e.g., battery 106, when the illumination system is in the stowed position. Moving the at least one UV illumination system includes lowering the UV illumination system below a top surface, e.g. top surface 126, of the trolley along a longitudinal axis, e.g. longitudinal axis A, to the stowed position. Moving the at least one UV illumination system includes elevating the UV illumination system above the top surface of the trolley along a longitudinal axis to the deployed position. The method includes activating at least one motor, e.g. motor 124, operatively connected to at least wheel, e.g. wheel 108, of the trolley housing to move the trolley housing along an aisle.

The method includes activating a second UV illumination system, e.g. UV illumination system 120, mounted in the trolley housing above a drawer, e.g. drawer 104, to illuminate surfaces of objects in the drawer with UV illumination. Activating the UV illumination system includes activating the UV illumination systems, e.g. systems 102 or 120, to emit UVC illumination with a wavelength ranging from 200 to 280 nm. In some embodiments, activating the UV illumination systems include activating the UV illumination system to emit UVC illumination with a wavelength of 222 nm.

The system/method provides means to disinfect/decontaminate the cabin to minimize the spread of pathogens, e.g. viral pathogens, due by disinfection of the cabin using UV light. This also provides a system standard with the actual trolley sizes and requirements and if no space available in the aircraft also provides a flexible off-wing version.

The methods and systems of the present disclosure, as described above and shown in the drawings, provide for a system standard with the actual trolley sizes and requirements having improved means to disinfect/decontaminate the cabin to minimize spread of pathogens. Improved on demand disinfection can minimize the spread of contaminants within an aircraft cabin, for example during a flight. While the apparatus and methods of the subject disclosure have been shown and described, those skilled in the art will readily appreciate that changes and/or modifications may be made thereto without departing from the scope of the subject disclosure.

What is claimed is:

1. A method comprising:
   moving at least one ultra-violet (UV) illumination system between a stowed position within an internal cavity of a trolley housing to a deployed position extended from the internal cavity;
   activating the UV illumination system in the extended position to disinfect an area external to the internal cavity of the trolley; and
   activating a second UV illumination system mounted in the trolley housing above a drawer to illuminate surfaces of objects in the drawer with UV illumination.

2. The method as recited in claim 1, wherein activating the UV illumination system includes activating the UV illumination system for a threshold period of time.

3. The method as recited in claim 1, further comprising charging the UV illumination system with a battery when the illumination system is in the stowed position.

4. The method as recited in claim 1, wherein moving the at least one UV illumination system includes lowering the UV illumination system below a top surface of the trolley along a longitudinal axis to the stowed position.

5. The method as recited in claim 1, wherein moving the at least one UV illumination system includes elevating the UV illumination system above a top surface of the trolley along a longitudinal axis to the deployed position.

6. The method as recited in claim 1, further comprising activating at least one motor operatively connected to at least one wheel of the trolley housing to move the trolley housing along an aisle.

7. The method as recited in claim 1, wherein activating the UV illumination system includes activating the UV illumination system to emit UVC illumination with a wavelength ranging from 200 to 280 nm.

8. The method as recited in claim 1, wherein activating the UV illumination system includes activating the UV illumination system to emit UVC illumination with a wavelength of 222 nm.

\* \* \* \* \*